(12) United States Patent
Schneider

(10) Patent No.: US 7,900,545 B2
(45) Date of Patent: Mar. 8, 2011

(54) CRANK DRIVE SYSTEM OF A SHAFT OF A MICROTOME

(75) Inventor: Volker Schneider, Sinsheim-Weiler (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 627 days.

(21) Appl. No.: 11/764,902

(22) Filed: Jun. 19, 2007

(65) Prior Publication Data

US 2008/0000339 A1  Jan. 3, 2008

(30) Foreign Application Priority Data

Jul. 3, 2006 (DE) .................. 10 2006 031 136

(51) Int. Cl.
*G01N 1/04* (2006.01)
*F16H 3/08* (2006.01)
*F16H 3/14* (2006.01)

(52) U.S. Cl. ............. 83/915.5; 83/412; 83/703; 83/167; 74/406; 74/397

(58) Field of Classification Search .......... 83/915.5, 83/167, 703, 709, 710, 711, 713, 412; 74/404, 74/406, 395–397, 355, 378, 423
See application file for complete search history.

(56) References Cited

U.S. PATENT DOCUMENTS

| | | | | |
|---|---|---|---|---|
| 1,853,919 A | * | 4/1932 | More | 68/255 |
| 2,190,856 A | * | 2/1940 | Young | 74/473.36 |
| 2,201,242 A | * | 5/1940 | Perkins | 74/387 |
| 2,331,168 A | * | 10/1943 | Breckenridge | 74/473.1 |
| 2,525,392 A | * | 10/1950 | Bee | 74/378 |
| 2,623,490 A | * | 12/1952 | Kiekhaefer | 440/75 |
| 2,795,998 A | * | 6/1957 | Gorham et al. | 83/411.3 |
| 2,829,612 A | * | 4/1958 | Schwartz | 112/162 |

(Continued)

FOREIGN PATENT DOCUMENTS

DE  898365  11/1953

(Continued)

OTHER PUBLICATIONS

Feather Safety Razor Co. LTD.; Microtome; Abstract of JP2005077369; Mar. 24, 2005; 1 page.

(Continued)

*Primary Examiner* — Laura M. Lee
(74) *Attorney, Agent, or Firm* — Hodgson Russ LLP

(57) ABSTRACT

A crank drive system (10) of a shaft (11) of a microtome (1) encompasses a first and a second shaft (11, 12). The first shaft (11) is rotatable with a crank (13) and comprises a first transfer gear (14). The second shaft (12) comprises a second transfer gear (15). A rotation of the first shaft (11) is transferable from the first transfer gear (14) to the second transfer gear (15) to cause the second shaft (12) to rotate. To make possible, with a microtome (1), an advance or a lowering of the specimen (2) in two respective oppositely directed rotation directions with the same crank drive system (10), the crank drive system (10) is characterized in that a third transfer gear (16) is provided. The first transfer gear (14) is selectably engageable with the second transfer gear (15) or with the third transfer gear (16) so that as a result, while the rotation direction of the second shaft (12) is maintained, the rotation direction of the first shaft (11) is reversible.

15 Claims, 6 Drawing Sheets

U.S. PATENT DOCUMENTS

| | | | |
|---|---|---|---|
| 2,940,322 A * | 6/1960 | Uhing | 74/22 R |
| 3,212,379 A * | 10/1965 | McCormick et al. | 83/167 |
| 3,261,229 A * | 7/1966 | Thomas et al. | 74/665 GB |
| 3,269,497 A * | 8/1966 | Bergstedt | 192/51 |
| 3,293,972 A * | 12/1966 | Imhof et al. | 83/414 |
| 3,611,875 A * | 10/1971 | Wistedt et al. | 409/288 |
| 3,628,386 A * | 12/1971 | Blum | 74/89.14 |
| 3,812,736 A * | 5/1974 | Nickstadt | 74/404 |
| 3,828,641 A * | 8/1974 | Sitte | 83/703 |
| 4,118,996 A * | 10/1978 | Eichinger | 74/404 |
| 4,460,075 A * | 7/1984 | Sommer | 192/18 A |
| 4,527,441 A * | 7/1985 | Nakahama | 74/378 |
| 4,598,621 A * | 7/1986 | Weinhold | 83/731 |
| 4,651,938 A * | 3/1987 | Memminger et al. | 242/564.5 |
| 4,741,192 A * | 5/1988 | Wallis | 72/187 |
| 5,065,657 A * | 11/1991 | Pfeifer | 83/703 |
| 5,117,706 A * | 6/1992 | Kempe | 74/441 |
| 5,671,648 A * | 9/1997 | Dern | 83/411.1 |
| 6,209,437 B1 * | 4/2001 | Izvoztchikov et al. | 83/707 |
| 7,685,899 B2 * | 3/2010 | Mowbray et al. | 74/329 |
| 2003/0060320 A1 | 3/2003 | Woodcock | |
| 2006/0037454 A1 * | 2/2006 | Hess | 83/575 |

FOREIGN PATENT DOCUMENTS

| | | |
|---|---|---|
| DE | 2253628 | 6/1973 |
| DE | 3539138 C1 | 8/1986 |
| DE | 3604029 C1 | 9/1986 |
| GB | 1532132 A | 11/1978 |
| GB | 2212570 A | 7/1989 |
| GB | 2419660 A | 5/2006 |

OTHER PUBLICATIONS

Leica Microsystems Nussloch GMBH, Leica SM2000 R Sliding Microtome Instruction Manual, version 2.1 English, Mar. 2004.

Chinese Office Action in Chinese counterpart Application No. 200710127323.7, Nov. 29, 2010.

* cited by examiner

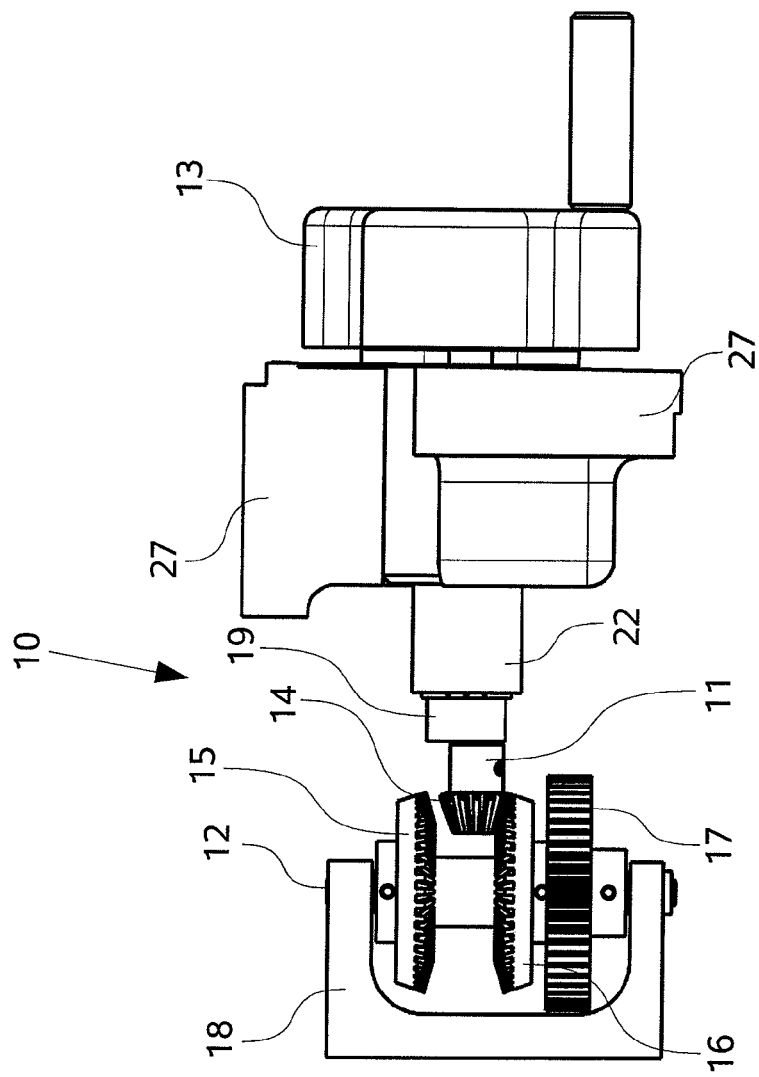
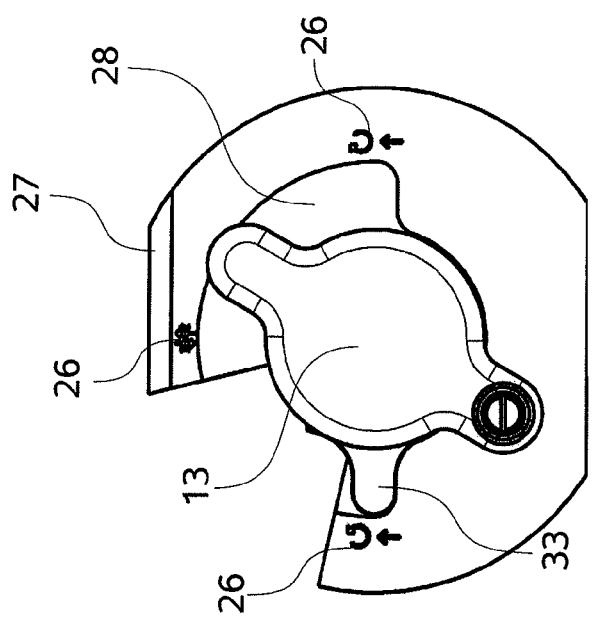
Fig. 4b
Fig. 4a

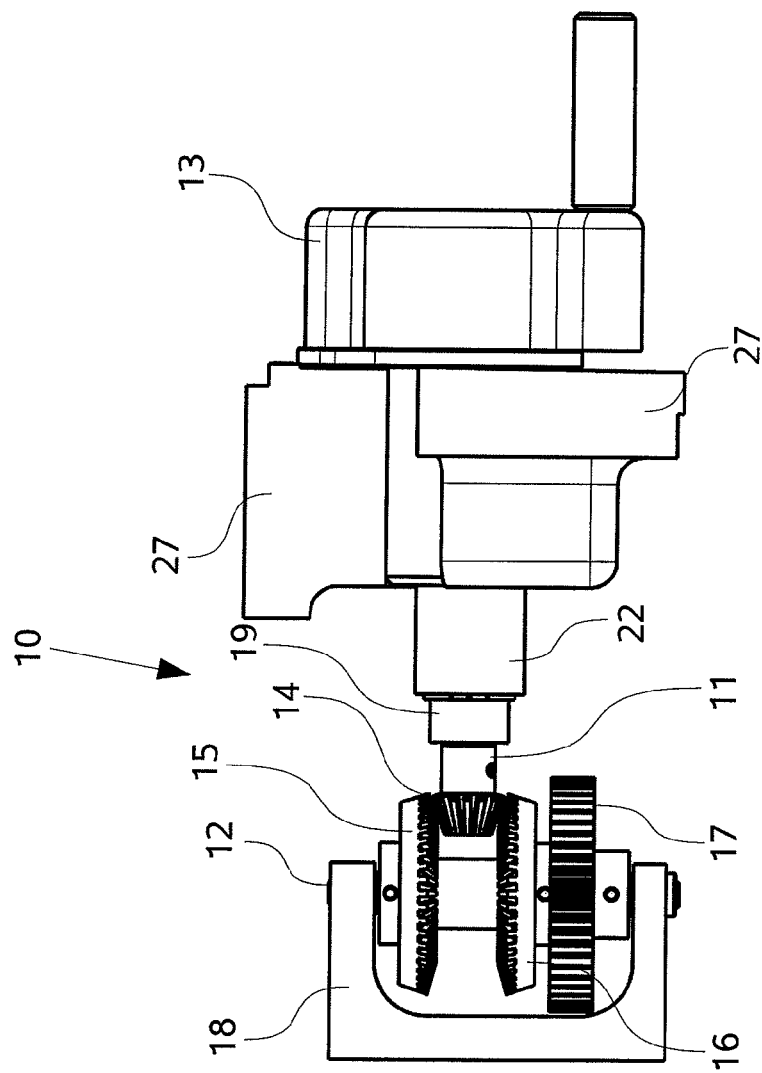
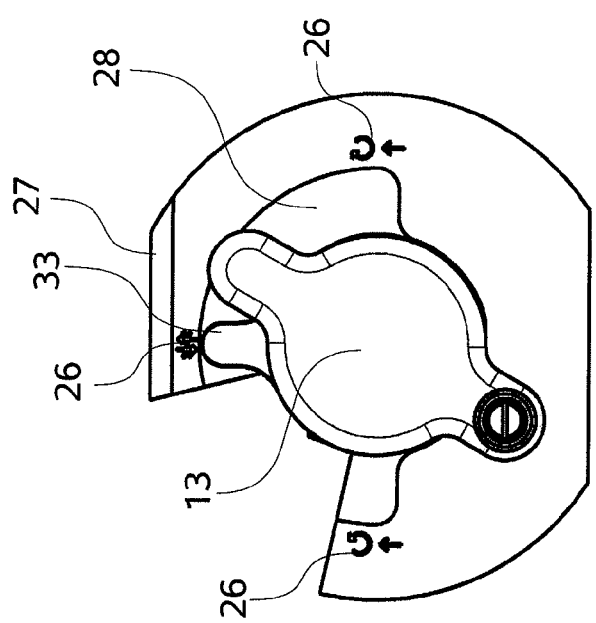
Fig. 5b
Fig. 5a

CRANK DRIVE SYSTEM OF A SHAFT OF A MICROTOME

CROSS REFERENCE TO RELATED APPLICATIONS

This application claims priority of German patent application 10 2006 031 136.1 filed Jul. 3, 2006, which is incorporated by reference herein.

FIELD OF THE INVENTION

The present invention relates to a crank drive system of a shaft of a microtome. More particularly, the invention relates to a microtome crank drive system of a type comprising a first and a second shaft or axle. The first shaft is rotatable with a crank and comprises a first transfer means. The second shaft comprises a second transfer means. A rotation of the first shaft is transferable from the first transfer means to the second transfer means of the second shaft. The second shaft can thereby capable of being caused to rotate. The first transfer means is usually joined in permanently nonrotatable fashion to the first shaft. In similar fashion, the second transfer means is joined in permanently nonrotatable fashion to the second shaft.

BACKGROUND OF THE INVENTION

The aforesaid crank drive system of a shaft of a microtome is used in particular in the context of a sliding microtome of the Applicant, namely in the "Leica SM2000R" model. This sliding microtome is described in printed form in a company brochure of March 2003. In a sliding microtome, the knife that sections the specimen is moved back and forth on a movably arranged slide in order to section the specimen arranged in a specimen holder. The specimen holder is moved vertically onto the knife via a corresponding mechanism, namely a micrometer mechanism; this is also referred to as "advance." The increment with which the specimen is advanced toward the knife can be set to an accuracy of 0.5 μm via a rotary knob fitted with a scale. Provided on the aforementioned sliding microtome as a further operating element is a crank with which a coarse drive mode for specimen movement toward the knife or away from the knife, i.e. substantially in a vertical direction, can be realized. It is possible as a result, after a sample change, to advance the specimen holder along with the specimen rapidly onto the knife, so that sectioning operations with a definable desired cut thickness can directly follow one another. Provided as a further operating element is a lever (activation lever), guided in an elongated hole and having a knob, with which a manual advance motion of the specimen holder toward the knife can be activated. This knob or lever is usually utilized only in the context of advance in sectioning mode, the advance occurring at the increment currently set using the rotary knob fitted with the scale. This sliding microtome also encompasses an operating state with automatic advance, the operating element relevant thereto being arranged on the microtome slide. This automatic advance is usually utilized upon initial cutting of the sample, and replaces actuation of the activation lever.

With regard to the crank drive system for coarse drive, it is at present possible to produce an advance only upon a clockwise rotation. Correspondingly, upon a counterclockwise rotation of the crank drive system, the specimen or specimen holder is moved away from the knife or lowered. It may, however, be desirable to allow an advance of the specimen also to be produced with a counterclockwise rotation, for example because different operators operate a single sliding microtome, and one operator is left-handed and another operator right-handed. Such a requirement at present can be met only by making available two different sliding microtomes, specifically such that with the one sliding microtome an advance is produced by rotating the crank clockwise, and in the case of the other sliding microtome a counterclockwise rotation of the crank produces a respective advance. The rotation direction of the crank drive system is therefore permanently defined in terms of the design.

SUMMARY OF THE INVENTION

It is therefore the object of the present invention to describe and further develop a crank drive system of a shaft of a microtome, in particular a sliding microtome, with which, in the same microtome, an advance or a lowering of the specimen in coarse drive mode is made possible with two respective opposite rotation directions using the same crank drive system.

The crank drive system according to the present invention of the kind cited initially achieves the aforesaid object by way of the features described herein. According thereto, a crank drive system of this kind is characterized in that a third transfer means is provided. The third transfer means could also be joined in permanently nonrotatable fashion to the second shaft. The first transfer means is selectably engageable with the second transfer means or with the third transfer means, so that as a result, while the rotation direction of the second shaft is maintained, the rotation direction of the first shaft is reversible. In other words, a rotation direction reversal of the first shaft is possible by bringing the first transfer means selectably into engagement with the second or the third transfer means, so that as a function of the currently existing engagement situation of the two participating transfer means, the specimen can be advanced with a clockwise rotation of the crank or with a counterclockwise rotation of the crank.

What has been recognized according to the present invention is firstly that it is not necessary to provide two microtomes of differing design configuration, specifically in order to provide for a left-hander, for example, a microtome that he or she can operate optimally. Instead an additional mechanism is made available for the coarse drive mechanism that has already been discussed; this additional mechanism makes possible a switchover of the rotation direction of the first shaft while retaining the rotation direction of the second shaft. This additional mechanism encompasses substantially the third transfer means and means that enable the first transfer means to be brought selectably into engagement with the second or the third transfer means.

As a result of this action, which in this individual case can be provided relatively simply and inexpensively, in very particularly advantageous fashion a single microtome can be made available that has the desired additional functionality, namely implementing a coarse drive mode for specimen advance in selectably adjustable fashion in both rotation directions. It is thus no longer necessary to procure two microtomes of almost identical design each merely having a different rotation direction, which cannot be switched over, for coarse drive.

In a particularly preferred embodiment, the transfer means are embodied in such a way that the first transfer means is positively engageable with the second transfer means or with the third transfer means. With a positive transfer of rotary motion, it can usually be assumed that the rotation performed at the crank by the operator will be transferred from the first shaft to the second shaft without slippage and other transfer losses. A gearwheel pair is fundamentally suitable in each case as a positive transfer means, the first transfer means comprising a type of gear that is embodied in substantially complementary fashion to the gear type of the second or third transfer means. Concretely, the first, second, and/or third transfer means could respectively comprise a gear, a bevel gear, a spur gear, a helical gear wheel, a worm gear or a worm or worm shaft, with the stipulation that the first transfer means is engageable in substantially complementary fashion with the second and the transfer means, and that the first transfer means meshes with the second or third transfer means.

In a further embodiment, the transfer means could be embodied in such a way that the first transfer means is nonpositively engageable with the second or third transfer means. Slippage losses in the transfer of rotary motion from the first shaft to the second shaft can occur in this context. This could, however, be advantageous when the specimen is being advanced from below toward the knife and the knife is positioned directly above the specimen, and is moved farther upward without attention by the operator, so that the specimen becomes pressed against the knife and in some circumstances is damaged. In this case a further advance of the specimen could be prevented as a function of the properties to be selected for the nonpositive transfer, specifically if the specimen or specimen holder cannot be moved farther upward because of a resistance. Concretely, the first, second, and/or third transfer means could comprise a wheel having a surface with a high coefficient of friction or one commensurate with the properties just mentioned.

It is conceivable in principle for the selectable engagement of the first transfer means with the second or the third transfer means to be implemented comparably with a transmission shifting point. In this case specifically, the second and third transfer means, for example, could be embodied in the form of an idler gear, in other words not be joined in permanently nonrotatable fashion to the second shaft. With a shift bushing joined nonrotatably to the second shaft, which bushing could be arranged between the second and the third transfer means, the second or the third transfer means could be connected nonrotatably to the second shaft as a function of the position of the shift bushing. In this case the first transfer means is constantly in engagement with the second and the third transfer means, and a rotation of the first shaft is always and directly transferred to the second and the third transfer means. Depending on the position of the shift bushing, the rotation of the first shaft is transferred to the second shaft via the second transfer means or via the third transfer means. If the shift bushing is in a neutral position, in which a nonrotatable connection does not exist between the second shaft and either the second or the third transfer means, the two shafts are mechanically decoupled.

As an alternative to a switchover system similar to a transmission shifting point, the first shaft could be movable relative to the second shaft, by means of a translating motion, in such a way that the first transfer means is thereby selectably engageable with the second or the third transfer means. In other words the entire shaft, and in some circumstances the crank secured thereon, is thus subjected to the translating motion. Corresponding guidance means arranged on the housing of the microtome are provided for this purpose, so that the translating motion of the shaft is possible in reproducible and purposeful fashion. This translating motion could be substantially a straight-line motion, although any displacement motions (depending on the design-related boundary conditions present in each case) are conceivable. It would also be conceivable in this connection for one shaft to be arranged tiltably or pivotably, in such a way that the first transfer means is thereby selectably engageable with the second or the third transfer means. The tilt or pivot axis would in this case be oriented or arranged around an axis transverse to the longitudinal direction of the tilted or pivoted shaft.

In a particularly preferred embodiment, the first shaft is movable relative to the second shaft, by means of a rotary or pivoting motion, in such a way that the first transfer means is thereby selectably engageable with the second or the third transfer means. The entire shaft is rotated or pivoted in this context, specifically about a rotation or pivot axis that is arranged substantially parallel to the longitudinal direction of the rotatably or pivotably arranged shaft, and laterally offset therefrom.

In terms of design, a rotary motion of the first shaft could be capable of implementation by way of a rotation of an eccentric sleeve, if the first shaft is rotatably mounted in the eccentric sleeve in an eccentric position. A physical embodiment of this kind is inexpensive and can be achieved economically with relatively simple means. The extent of the eccentric arrangement of the shaft in the eccentric sleeve will depend in general on the physical arrangement of the second and the third transfer means, specifically so that by way of a rotation of the eccentric sleeve, the first transfer means can be brought selectably into engagement with the second or the third transfer means.

For manual actuation, the eccentric sleeve could be joined nonrotatably to a shifting plate actuable by an operator. Provision could furthermore be made for the eccentric sleeve to be rotatably mounted directly in a bearing of the microtome housing or in a bushing, the bushing being secured in stationary fashion on the housing of the microtome. The shaft could in this context be combined with the transfer means, eccentric sleeve, and bushing into one modular assembly, thus considerably simplifying fabrication and production of a microtome.

The shifting plate and eccentric sleeve could then be embodied in such a way that upon a rotation of the shifting plate through an angle less than or equal to 270 degrees, preferably 180 degrees, the crank drive system is conveyable from a first operating state to a second operating state. In the first operating state the first transfer means is in engagement with the second transfer means, and in the second operating state the first transfer means is in engagement with the third transfer means. In other words, a switchover between the two operating states should be possible by rotation of the shifting plate through a relatively small angle and not through several complete revolutions, specifically so that the switchover can be performed manually by the operator in rapid and simple fashion.

End stops that limit the rotation of the shifting plate or of the eccentric sleeve could additionally be provided. For example, the first operating state could be established in the position of the one end stop, and the second operating state established in the position of the second end stop. A snap-locking means, as well as at least two snap-locked positions corresponding to the two operating states, could furthermore be provided, specifically in order to ensure that the shifting plate or eccentric sleeve remains in the position that corresponds to the respective operating state established by the operator.

In a very particularly preferred embodiment, an operating state is provided in which the first transfer means is in engagement with neither the second transfer means nor the third transfer means. A snap-locked position could likewise be allocated to this operating state. In this operating state the first shaft is mechanically decoupled from the second shaft so that, in the context of later sectioning and the very small advances (on the order of 1 μm) associated therewith, no blockage or disruption of the advance is caused by frictional losses or resistances of the crank or the first shaft. In this connection, no blockage of an advance motion occurs even if the operator inadvertently immobilizes the crank and thus the first shaft.

The first shaft could be joined nonrotatably to a crank. The shaft accordingly rotates, for example, through one-half revolution if the crank is likewise rotated through one-half revolution. Alternatively, a rotary motion of the crank could be transferable to the first shaft or to the first transfer means via an intermediate transmission stage having a definable step-down or step-up ratio. In this case the step-up ratio could be selected in such a way that, for example, the shaft is rotated through two complete revolutions if the crank is manually rotated by the operator through one complete revolution. The selection of the step-up ratio will generally depend on the other physical properties of the micrometer mechanism and on the mechanical drive system coacting therewith.

There are various ways of advantageously embodying and refining the teaching of the present invention. The reader is referred, for that purpose, on the one hand to the claims, and on the other hand to the explanation below of the preferred exemplifying embodiments of the invention with reference to the drawings. In conjunction with the explanation of the preferred exemplifying embodiments of the invention with reference to the drawings, an explanation is also given of generally preferred embodiments and refinements of the teaching.

BRIEF DESCRIPTION OF THE DRAWINGS

In the drawings:

FIG. 4a is a schematic plan view of the crank and the shifting plate in a first shift position;

FIG. 4b is a schematic side view of the crank drive system according to the present invention in a first operating state;

FIG. 5a is a schematic plan view of the crank and the shifting plate in a second shift position;

FIG. 5b is a schematic side view of the crank drive system according to the present invention in a second operating state;

DETAILED DESCRIPTION OF THE INVENTION

Figure 1:
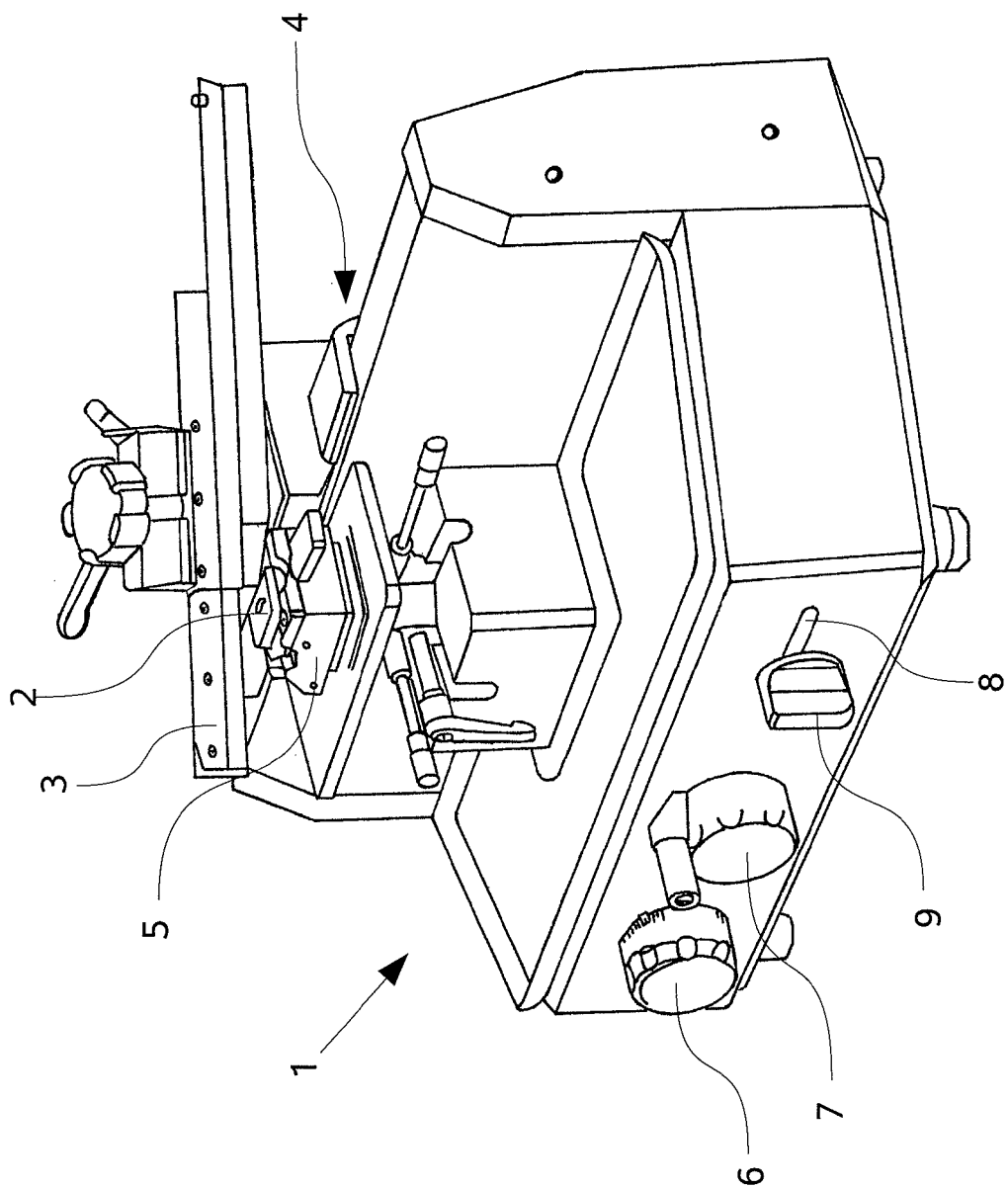
FIG. 1 is a perspective view of a sliding microtome known from the existing art.

Identical or similar components and assemblies are labeled in the Figures with the same reference characters.

FIG. 1 shows a sliding microtome 1 of the Applicant, namely the "Leica SM2000 R" model. This sliding microtome is already known from the existing art and does not comprise a crank drive system according to the present invention. In sliding microtome 1, knife 3 that sections specimen 2 is moved back and forth on a movably arranged slide 4 in order to section specimen 2 arranged in specimen holder 5. Specimen 2 is usually a histological preparation that is embedded in a paraffin block and is clamped into specimen holder 5. Specimen holder 5 is moved vertically onto knife 3 via a corresponding mechanism, namely a micrometer mechanism provided in the housing of sliding microtome 1 and not shown in FIG. 1. The increment with which specimen 2 is advanced upward toward knife 3 can be set, to an accuracy of 0.5 μm, via a rotary knob 6 fitted with a scale. Provided on sliding microtome 1 shown in FIG. 1 as a further operating element is a crank 7 with which a coarse drive mode for movement of the specimen toward knife 3 or away from knife 3 (i.e. substantially in a vertical direction) can be implemented. This makes it possible, after a sample change, to advance specimen holder 5 along with specimen 2 rapidly onto knife 3, so that the sectioning operations at a definable desired cut thickness can directly follow one another. Provided as a further operating element is an activation lever 9, guided in an elongated hole 8, with which a manual advancing motion of specimen holder 5 toward knife 3 can be activated. Activation lever 9 is usually utilized only in the context of advance in sectioning mode; the advance occurs with the increment currently set on rotary knob 6 fitted with the scale. This sliding microtome 1 also encompasses an operating state with automatic advance, the operating element relevant thereto being arranged on microtome slide 4, specifically on the back side (not visible in FIG. 1) of slide 4. This automatic advance is usually utilized upon initial cutting of the sample, and replaces actuation of activation lever 9.

Figure 2:
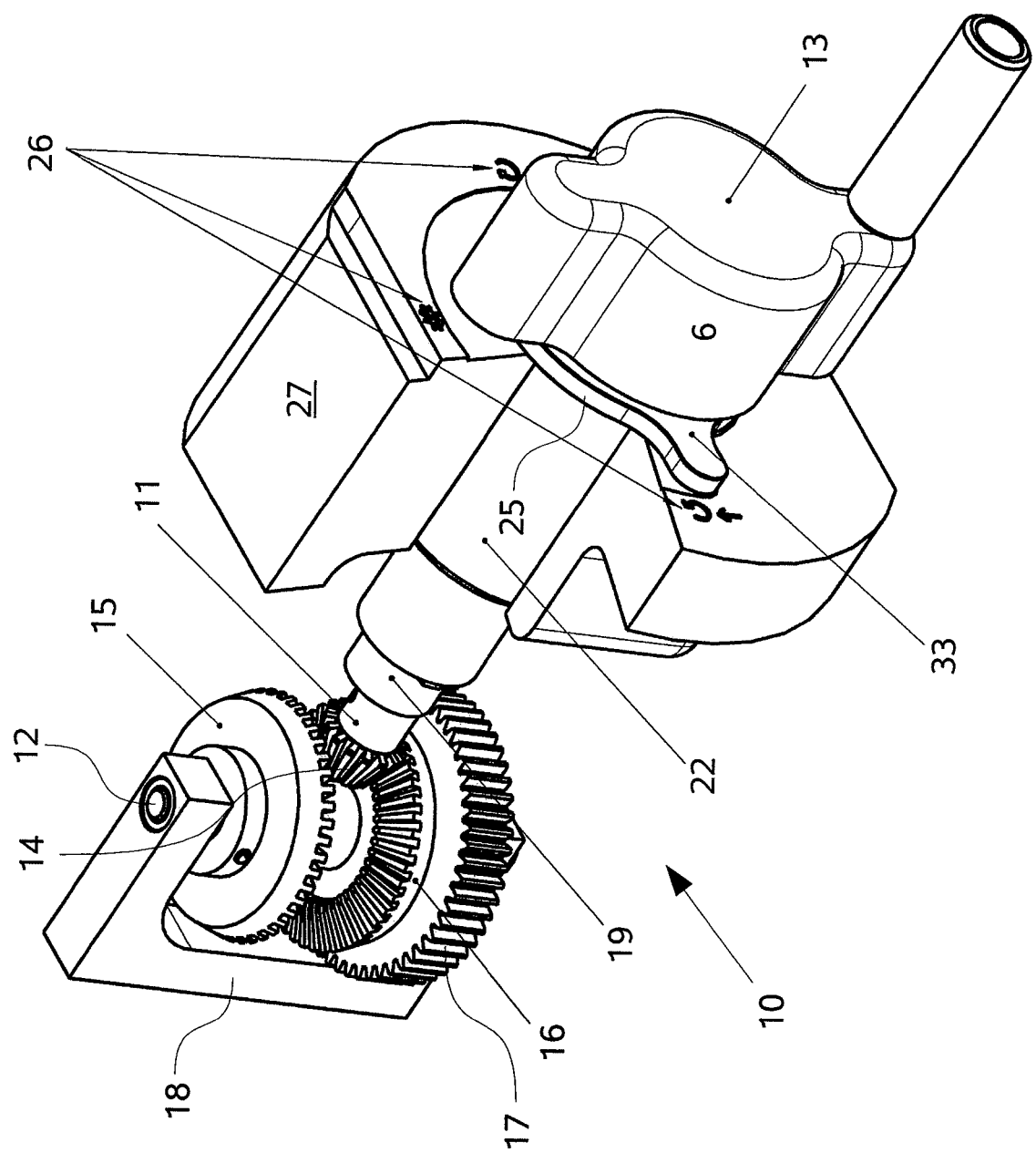
FIG. 2 schematically depicts a perspective view of a crank drive system according to the present invention of a shaft of a microtome.

FIG. 2 is a perspective view of crank drive system 10 according to the present invention that can be used in sliding microtome 1 of FIG. 1. Crank drive system 10 comprises a first shaft 11 and, arranged substantially perpendicular thereto, a second shaft 12. First shaft 11 is rotatable manually by an operator using crank 13. First shaft 11 comprises a first transfer means 14, which is embodied in the form of a small bevel gear and which, for the sake of simplicity, will likewise be identified hereinafter by the reference character 14. Small bevel gear 14 is joined nonrotatably to first shaft 11. Second shaft 12 comprises a second transfer means 15 that is embodied in the form of a large bevel gear. Large bevel gear 15 is joined nonrotatably to second shaft 12. The tooth set of large bevel gear 15 faces toward small bevel gear 14.

According to the present invention, a third transfer means 16 is provided which is embodied in the form of a large bevel gear and, in this exemplifying embodiment, is joined nonrotatably to second shaft 12. Both the second and the third transfer means 15, 16 are, for the sake of simplicity, hereinafter respectively identified by reference characters 15 and 16. The tooth set of large bevel gear 16 likewise faces toward small bevel gear 14. It is possible to bring small bevel gear 14 into engagement with large bevel gear 16 (i.e. the third transfer means) or with large bevel gear 15 (i.e. the second transfer means). In the first case, small bevel gear 14 accordingly meshes with large bevel gear 16, so that in this operating state a rotation of shaft 11 is transferred via small bevel gear 14 to large bevel gear 16 of second shaft 12, and second shaft 12 is thereby also rotated. If crank 13 of FIG. 2 is therefore rotated counterclockwise (looking at crank 13 from the front), shaft 11 likewise rotates counterclockwise, and large bevel gear 16 and second shaft 12 rotate counterclockwise (looking from above at large bevel gears 15 and 16). With this rotation direction of second shaft 12, specimen holder 5 (not shown in FIG. 2) is moved or advanced vertically upward toward knife 3 of sliding microtome 1. If small bevel gear 14 is then brought into meshing engagement with large bevel gear 15, crank 13 of FIG. 2 can thus be rotated clockwise (once again looking at crank 13 from the front). Shaft 11 likewise rotates clockwise and, in this case as well, large bevel gear 15 and second shaft 12 rotate counterclockwise (once again looking at large bevel gear 15 from above). The spur gear indicated with reference character 17 in FIG. 2 is of no further significance for crank drive system 10 according to the present invention. Second shaft 12 is rotatably mounted in bearing block 18. Shaft 12 drives the micrometer mechanism (not shown in the Figure) of the microtome indirectly via spur gear 17.

Transfer means 14, 15, and 16 are embodied in such a way that first transfer means 14 can be brought into positive engagement with second transfer means 15 or with third transfer means 16.

First shaft 11 is movable relative to second shaft 12 by means of a rotary motion, in such a way that the first transfer means, or small bevel gear 14, can thereby be selectably brought into engagement with the second transfer means (large bevel gear 15) or with the third transfer means (large bevel gear 16). The manner in which this is implemented in detail in terms of design, in the exemplifying embodiment of the present invention shown in FIG. 2, is evident from the schematic sectioned view of FIG. 3.

Figure 3:
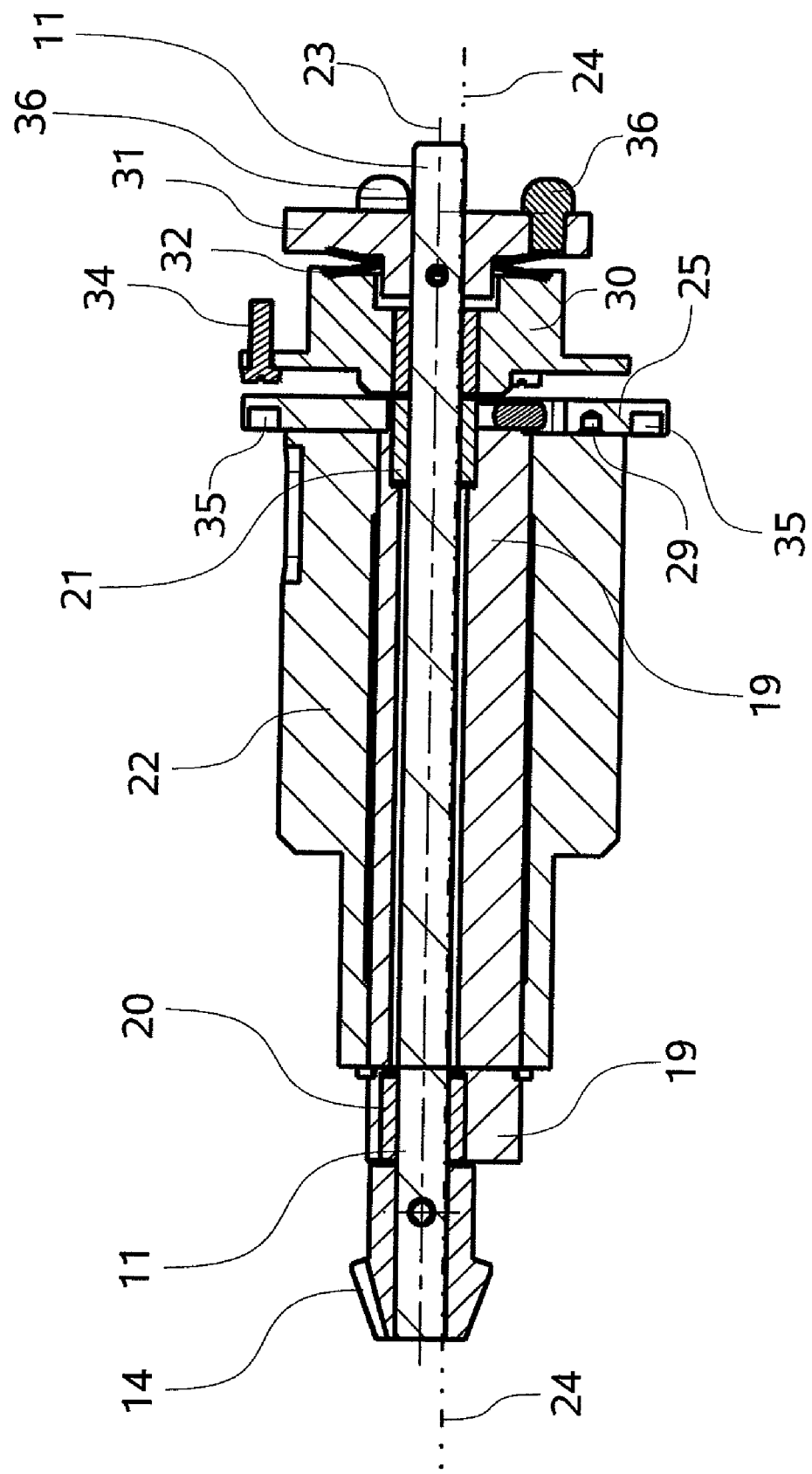
FIG. 3 is a schematic sectioned view of part of the crank drive system according to the present invention.

First shaft 11 is rotatably mounted in eccentric sleeve 19 and can be rotated relative to eccentric sleeve 19 and independently thereof. The two plain bearings 20, 21 are provided for this purpose. Eccentric sleeve 19 is in turn rotatably mounted in a bushing 22 that can be installed in stationary fashion on a housing part 27 of the microtome. First shaft 11 is arranged in an eccentric position in eccentric sleeve 19, specifically in such a way that rotation axis 23 around which first shaft 11 is rotated exhibits a parallel offset from the central longitudinal axis 24 of eccentric sleeve 19. Longitudinal axis 24 of eccentric sleeve 19 is drawn in extended fashion, and is located on the lower rim (as drawn in FIG. 3) of shaft 11, so that longitudinal axis 24 is not visible there. Because of the eccentric arrangement of shaft 11 in eccentric sleeve 19, upon rotation of eccentric sleeve 19, shaft 11 is subjected to a rotary motion around longitudinal axis 24 of eccentric sleeve 19, so that small bevel gear 14 can be brought into engagement with large bevel gear 15 or with large bevel gear 16, depending on the rotational state of eccentric sleeve 19. FIG. 3 further shows that small bevel gear 14 is joined nonrotatably to shaft 11.

Eccentric sleeve 19 is nonrotatably joined to a shifting plate 25 that can be actuated by an operator. Shifting plate 25 and eccentric sleeve 19 are embodied in such a way that upon a rotation of shifting plate 25 through an angle of 180 degrees, crank drive system 10 can be conveyed from a first operating state to a second operating state. In the first operating state, small bevel gear 14 is in engagement with large bevel gear 15. In the second operating state, small bevel gear 14 is in engagement with large bevel gear 16.

Figure 6B:
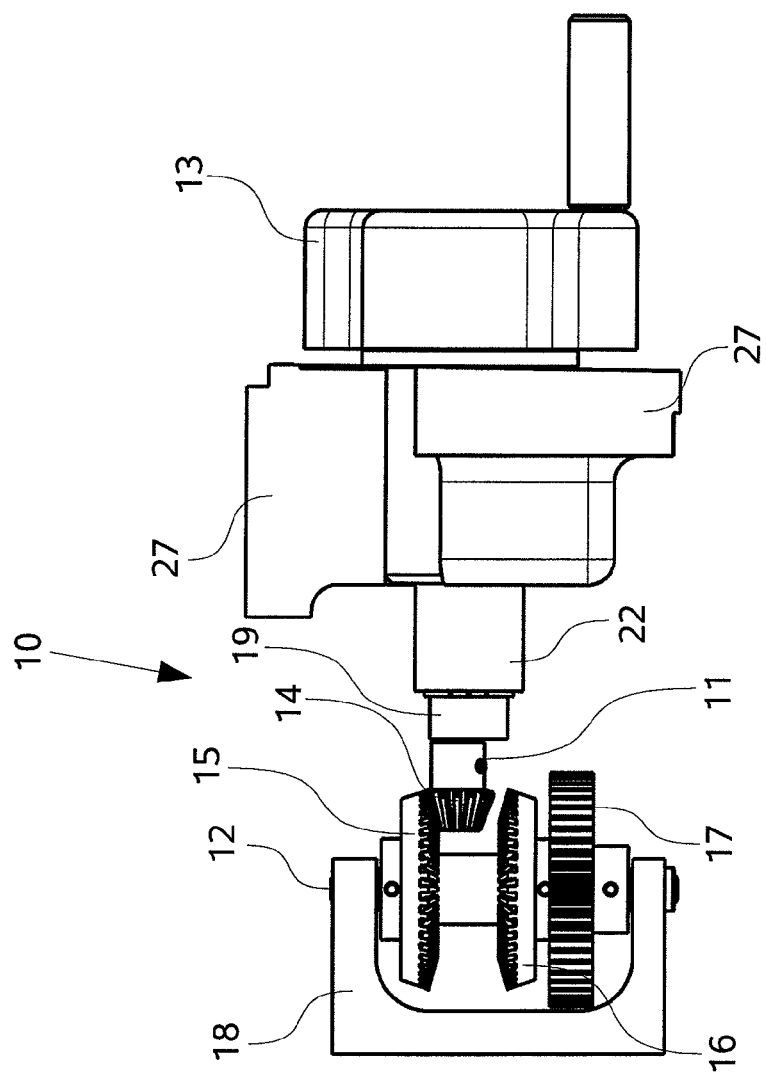
FIG. 6b is a schematic side view of the crank drive system according to the present invention in a third operating state.
Figure 6A:
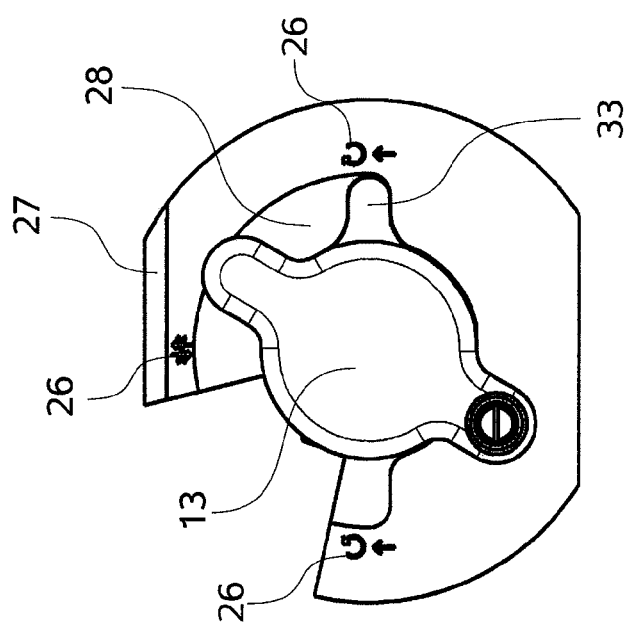
FIG. 6a is a schematic plan view of the crank and the shifting plate in a third shift position.

FIGS. 4a, 5a, and 6a each show a plan view of crank 13 and of shifting plate 25. Shifting plate 25 is shown in three different respective positions which correspond to the three operating states provided for crank drive system 10 according to the present invention. FIGS. 4b, 5b, and 6b, arranged alongside, respectively show side views of crank drive system 10 according to the present invention in the operating states that correspond respectively to the shift positions of shifting plate 25 that are shown in FIGS. 4a, 5a, and 6a.

For example, the position of shifting plate 25 in FIG. 4a corresponds to the position shown in FIG. 2. Correspondingly, when crank 13 is rotated counterclockwise, shaft 11 and small bevel gear 14 likewise rotate counterclockwise. Small bevel gear 14 is in meshing engagement with large bevel gear 16. The result of this in turn is that large bevel gear 16 is rotated counterclockwise (looking from above at shaft 12). A rotation of second shaft 12 in this rotation direction produces an advance of specimen 2 toward knife 3. This relationship is also indicated by symbol 26 arranged at the left, toward which grip element 33 of shifting plate 25 points in FIG. 4a.

The position of shifting plate 25 in FIG. 5a corresponds to the operating state in which first shaft 11 is decoupled from second shaft 12, and small bevel gear 14 is not in engagement with either large bevel gear 15 or large bevel gear 16. Even if crank 13 were to be rotated in this operating state, this rotation will not be transferred to shaft 12. This operating state is shown in the side view in FIG. 5b. This relationship is also indicated by symbol 26 arranged at the top center, toward which grip element 33 of shifting plate 25 points in FIG. 5a.

When shifting plate 25 is in the position according to FIG. 6a, small bevel gear 14 is in meshing engagement with large bevel gear 15. Correspondingly, when crank 13 is rotated clockwise, shaft 11 and small bevel gear 14 likewise rotate clockwise. Large bevel gear 15 and shaft 12 are thus rotated counterclockwise (looking from above at shaft 12). A rotation of second shaft 12 in this rotation direction produces an advance of specimen 2 toward knife 3. This relationship is also indicated by symbol 26 arranged at the right, toward which grip element 33 of shifting plate 25 points in FIG. 6a.

Shifting plate 25 comprises an annular groove 35 extending over a half-circle, which groove is shown in the sectioned view of FIG. 3. Provided on housing part 27 and projecting from the outer surface is a pin (not shown) that engages into groove 35; end stops for the rotation range of shifting plate 25 are thereby implemented, namely from the one end position shown in FIG. 4a to the other end position shown in FIG. 6a. It is apparent from FIGS. 4a, 5a, and 6a that housing part 27 comprises, on its surface facing toward crank 13, a depression 28 that, inter alia, visually indicates the rotation range of shifting plate 25 and eccentric sleeve 19.

It is not shown in further detail in the Figures that a ball catch is provided in bushing 22, which catch snaps into three cutouts 29 (one of which is shown in FIG. 3) each offset 90 degrees. A snap-locking means and three snap-lock positions corresponding to the three operating states are thereby provided, so that shifting plate 25 and eccentric sleeve 19 remain in a position that corresponds to the particular operating state established by the operator.

In FIG. 3, screw 34 indicates that the cover of crank 13 shown in FIG. 2 can be secured onto component 30. Component 30 can be rotated with respect to shaft 11. Component 31 is joined nonrotatably to shaft 11. Two cup springs 32 are provided between component 30 and component 31. Cup springs 32 are preloaded in such a way that component 31 is forced away from component 30 and from small bevel gear 14 (connected via first shaft 11). Component 30 is thereby caused to abut against shifting plate 25, and can be moved very little in an axial direction. Component 31 engages positively, via ball pins 36, into the cover (not shown in FIG. 13) of crank 13, so that ultimately crank 13 is joined nonrotatably to shaft 11. In the event of excessive torque on crank 13, ball pins 36 (spring-loaded via component 31) slip out of the depressions in crank 13 and thus implement a slip clutch.

In conclusion, be it noted very particularly that the exemplifying embodiments discussed above serve merely to describe the teaching claimed, but do not limit it to the exemplifying embodiments.

Parts List

1 Sliding microtome or microtome
2 Specimen
3 Knife
4 Slide
5 Specimen holder
6 Rotary knob 7 Crank
8 Elongated hole
9 Activation lever for activating manual advance
10 Crank drive system
11 First shaft
12 Second shaft
13 Crank
14 First transfer means of (11)
15 Second transfer means of (12)
16 Third transfer means of (12)
17 Spur gear
18 Bearing block of (12)
19 Eccentric sleeve
20 Plain bearing in (19) for (11)
21 Plain bearing in (19) for (11)
22 Bushing in which (19) is rotatably mounted
23 Rotation axis of (11)
24 Central longitudinal axis of (19)
25 Shifting plate
26 Symbols identifying the respective operating state
27 Housing part of (1) in which (22) is installed
28 Depression on (27), end stop for (25)
29 Cutout on (25)
30 Component on which (13) can be secured
31 Component that is joined nonrotatably to (11) and engages positively into the cover of crank (13)
32 Cup springs
33 Grip element of (25)
34 Screw for fastening cover of (13) to (30)
35 Groove in (25) for limiting the rotation range
36 Ball pins on (31) for positive engagement into cover of crank (13)

What is claimed is:

1. A microtome comprising:
a knife;
a specimen holder;
a crank operably connected to the specimen holder for displacing the specimen holder relative to the knife;
a first shaft connected to the crank, the first shaft being rotatable by rotation of the crank;
a first transfer means associated with the first shaft for transmitting rotation of the first shaft;
a second shaft;
a second transfer means associated with the second shaft for transmitting rotation to the second shaft;
a third transfer means associated with the second shaft for transmitting rotation to the second shaft;
wherein the first transfer means is selectably engageable with either the second transfer means or the third transfer means to transmit rotation of the first shaft to the second shaft, whereby the second shaft is caused to rotate in an output rotational direction when the first transfer means is engaged with the second transfer means, and the output rotational direction remains the same when the rotational direction of the first shaft is reversed and the first transfer means is engaged with the third transfer means;
wherein the first shaft is movable relative to the second shaft to selectably engage the first transfer means with either the second transfer means or the third transfer means;
wherein the first shaft is movable relative to the second shaft in a rotary or pivoting motion to selectably engage the first transfer means with either the second transfer means or the third transfer means; and
wherein the first shaft is rotatably mounted in an eccentric sleeve, and the eccentric sleeve is rotatable to selectably engage the first transfer means with either the second transfer means or the third transfer means.

2. The crank drive system according to claim 1, wherein the first transfer means is positively engageable with the second transfer means or the third transfer means.

3. The crank drive system according to claim 2, wherein the first, second, and third transfer means comprise at least one element selected from the group consisting of a gear, a bevel gear, a spur gear, a helical gear wheel, or a worm gear or worm.

4. The crank drive system according to claim 1, wherein the first transfer means is nonpositively engageable with the second transfer means or the third transfer means.

5. The crank drive system according to claim 4, wherein the first transfer means is frictionally engageable with the second transfer means or the third transfer means.

6. The crank drive system according to claim 5, wherein at least one of the first transfer means, the second transfer means, and the third transfer means comprises a wheel including a surface having a high coefficient of friction.

7. The crank drive system according to claim 1, wherein the eccentric sleeve is joined nonrotatably to a shifting plate adjustable by an operator.

8. The crank drive system according to claim 1, wherein the eccentric sleeve is rotatably mounted in a bushing.

9. The crank drive system according to claim 7, wherein rotation of the shifting plate through an angle less than or equal to 270 degrees changes the crank drive system from a first operating state to a second operating state, in the first operating state the first transfer means being in engagement with the second transfer means, and in the second operating state the first transfer means being in engagement with the third transfer means.

10. The crank drive system according to claim 9, wherein the angle less than or equal to 270 degrees is 180 degrees.

11. The crank drive system according to claim 9, further comprising end stops arranged to limit rotation of the shifting plate or of the eccentric sleeve.

12. The crank drive system according to claim 9, further comprising snap-locking means defining a pair of snap-locked positions respectively corresponding to the first operating state and the second operating state, whereby the shifting plate or the eccentric sleeve is maintained in a position that corresponds to the corresponding operating state.

13. The crank drive system according to claim 12, wherein the crank drive system has a third operating state in which the first transfer means is in engagement with neither the second transfer means nor the third transfer means, and the snap-locking means defines a third snap-locked position corresponding to the third operating state.

14. The crank drive system according to claim 1, wherein the first shaft is joined nonrotatably to the crank.

15. A microtome comprising:
a knife;
a specimen holder;
a crank rotatable in clockwise and counterclockwise rotational directions;
a first shaft connected to the crank for rotation with the crank;
a first gear mounted on the first shaft to rotate with the first shaft;
a second shaft connected to the specimen holder such that rotation of the second shaft in an output rotational direction causes the specimen holder to advance toward the knife;
a second gear and a third gear each mounted on the second shaft;

a shifting plate for adjusting a position of the first shaft relative to the second shaft to selectably engage the first gear with either the second gear or the third gear to transmit rotational motion from the first shaft to the second shaft;

wherein the crank is operably connected to the specimen holder for displacing the specimen holder relative to the knife;

wherein the first shaft is movable relative to the second shaft in a rotary or pivoting motion to selectably engage the first gear with either the second gears or the third gear;

wherein the first shaft is rotatably mounted in an eccentric sleeve, and the eccentric sleeve is rotatable to selectably engage the first gear with either the second gear or the third transfer gear; and wherein rotation of the crank in a clockwise direction causes the second shaft to rotate in the output rotational direction when the first gear is engaged with the second gear, and rotation of the crank in a counterclockwise direction causes the second shaft to rotate in the output rotational direction when the first gear is engaged with the third gear.

* * * * *